(12) United States Patent
Miller et al.

(10) Patent No.: US 8,271,295 B1
(45) Date of Patent: Sep. 18, 2012

(54) HEALTH CLINIC BROKER

(75) Inventors: Deborah L. Miller, Kansas City, MO (US); Carl J. Persson, Olathe, KS (US); Thomas H. Wilson, Overland Park, KS (US)

(73) Assignee: Sprint Communications Company L.P., Overland Park, KS (US)

( * ) Notice: Subject to any disclaimer, the term of this patent is extended or adjusted under 35 U.S.C. 154(b) by 355 days.

(21) Appl. No.: 12/178,608

(22) Filed: Jul. 23, 2008

(51) Int. Cl.
*G06Q 10/00* (2012.01)

(52) U.S. Cl. .................. 705/2; 705/3; 705/80; 706/52; 709/204; 340/531

(58) Field of Classification Search .............. 705/2, 7, 705/8, 3, 7.19; 340/531; 709/204; 706/52
See application file for complete search history.

(56) References Cited

U.S. PATENT DOCUMENTS

| | | | |
|---|---|---|---|
| 5,933,136 A | 8/1999 | Brown | |
| 5,960,403 A | 9/1999 | Brown | |
| 5,995,937 A | 11/1999 | DeBusk et al. | |
| 6,345,260 B1* | 2/2002 | Cummings et al. | 705/7.19 |
| 6,389,454 B1* | 5/2002 | Ralston et al. | 709/204 |
| 6,663,846 B1 | 12/2003 | McCombs et al. | |
| 6,957,107 B2 | 10/2005 | Rogers et al. | |
| 7,337,123 B2* | 2/2008 | Dvorak et al. | 705/8 |
| 7,801,745 B2 | 9/2010 | Walker et al. | |
| 7,956,727 B2 | 6/2011 | Loncar | |
| 8,224,667 B1 | 7/2012 | Miller et al. | |
| 2002/0059082 A1* | 5/2002 | Moczygemba | 705/3 |
| 2002/0116220 A1* | 8/2002 | Glazier | 705/2 |
| 2002/0198454 A1 | 12/2002 | Seward et al. | |
| 2003/0036683 A1 | 2/2003 | Kehr et al. | |
| 2003/0144874 A1* | 7/2003 | Barret et al. | 705/2 |
| 2004/0010423 A1* | 1/2004 | Sameh | 705/2 |
| 2004/0122706 A1* | 6/2004 | Walker et al. | 705/2 |
| 2004/0193449 A1 | 9/2004 | Wildman et al. | |
| 2004/0199412 A1* | 10/2004 | McCauley | 705/7 |
| 2004/0236601 A1* | 11/2004 | Summers et al. | 705/2 |
| 2004/0260577 A1* | 12/2004 | Dahlin et al. | 705/2 |
| 2005/0068167 A1* | 3/2005 | Boyer et al. | 340/531 |
| 2005/0102159 A1 | 5/2005 | Mondshine | |
| 2005/0234741 A1* | 10/2005 | Rana et al. | 705/2 |
| 2006/0047552 A1* | 3/2006 | Larsen et al. | 705/8 |
| 2006/0053035 A1 | 3/2006 | Eisenberg | |
| 2006/0129444 A1* | 6/2006 | Baeza et al. | 705/8 |
| 2006/0161468 A1* | 7/2006 | Larsen et al. | 705/8 |
| 2006/0173713 A1 | 8/2006 | Petro et al. | |
| 2006/0271399 A1* | 11/2006 | Robson et al. | 705/2 |
| 2007/0015974 A1 | 1/2007 | Higgins et al. | |
| 2007/0073555 A1 | 3/2007 | Buist | |
| 2007/0168228 A1 | 7/2007 | Lawless | |

(Continued)

OTHER PUBLICATIONS

Google patents search.*

(Continued)

*Primary Examiner* — Dilek B Cobanoglu

(57) ABSTRACT

A health clinic broker system is provided. The system comprises at least one computer system and a health clinic broker application that, when executed on the at least one computer system, receives a plurality of health care service requests containing information about a health care need, at least some of the requests seeking to set an appointment for health care. The system also receives a plurality of health care service offerings and provides at least one recommendation for the appointment for health care based on matching the health care service offerings with the health care service request.

9 Claims, 7 Drawing Sheets

U.S. PATENT DOCUMENTS

| | | | |
|---|---|---|---|
| 2007/0226010 A1* | 9/2007 | Larsen | 705/2 |
| 2007/0282476 A1 | 12/2007 | Song et al. | |
| 2008/0005054 A1* | 1/2008 | Kurian et al. | 706/52 |
| 2008/0255880 A1 | 10/2008 | Beller et al. | |
| 2008/0312959 A1 | 12/2008 | Rose et al. | |
| 2009/0164236 A1* | 6/2009 | Gounares et al. | 705/2 |
| 2009/0248439 A1 | 10/2009 | Becker et al. | |

OTHER PUBLICATIONS

Miller, Deborah L., et al., Patent Application entitled, "Health Care Delivery Optimization," filed Jul. 31, 2008, U.S. Appl. No. 12/183,893.

Office Action dated Dec. 8, 2010, U.S. Appl. No. 12/183,893, filed Jul. 31, 2008.

Kumed, "Visit Your Physician Online", 2007, http://www.kumed.com/print.aspx?page_id=2370.

Final Office Action dated Mar. 31, 2011, U.S. Appl. No. 12/183,893, filed Jul. 31, 2008.

Advisory Action dated Jun. 8, 2011, U.S. Appl. No. 12/183,893, filed Jul. 31, 2008.

Google Patent Search TM with search criteria "healthcare monitoring and risk level and increasing frequency of messages to providers," dated Feb. 15, 2012.

Google Scholar Search TM with search criteria "medical provider does not timely respond to the alerting," dated Feb. 16, 2012.

Dialog® Search, dated Feb. 16, 2012, Scientific and Technical Information Center.

Notice of Allowance dated Feb. 21, 2012, U.S. Appl. No. 12/367,382, filed Feb. 6, 2009.

Miller, Deborah L., et al., Patent Application entitled, "Therapy Adherence Methods and Architecture," filed Feb. 6, 2009, U.S. Appl. No. 12/367,382.

Examiner's Answer dated Oct. 12, 2011, U.S. Appl. No. 12/183,893, filed Jul. 31, 2008.

Office Action dated Oct. 5, 2011, U.S. Appl. No. 12/367,382, filed Feb. 6, 2009.

* cited by examiner

FIG. 6
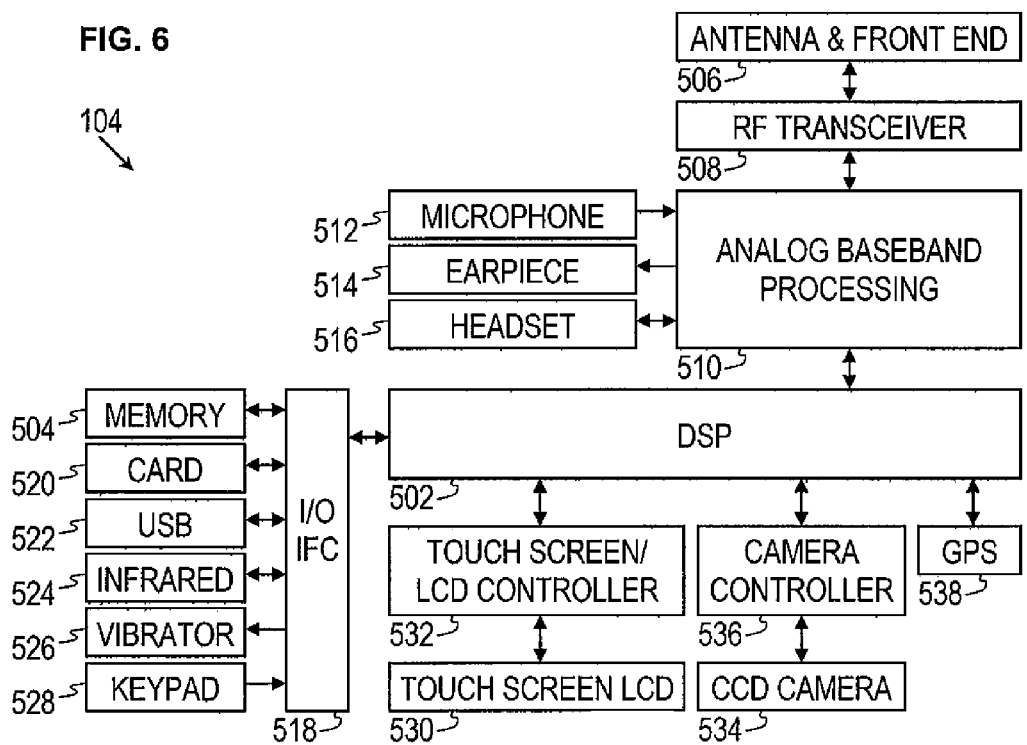
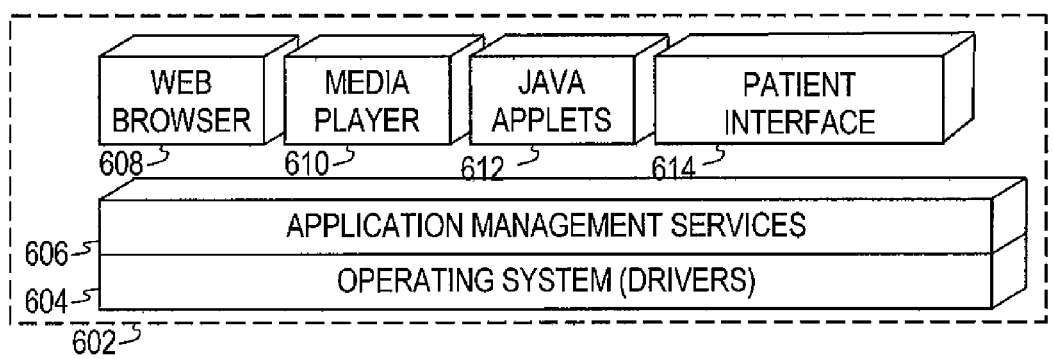
FIG. 7

HEALTH CLINIC BROKER

CROSS-REFERENCE TO RELATED APPLICATIONS

None.

STATEMENT REGARDING FEDERALLY SPONSORED RESEARCH OR DEVELOPMENT

Not applicable.

REFERENCE TO A MICROFICHE APPENDIX

Not applicable.

BACKGROUND

Patients seeking non-emergency medical care traditionally must phone their doctor, hospital, or other caregiver days or weeks in advance, briefly describe their condition to a receptionist, and receive an appointment date and time which may not be convenient. Patients needing emergency care visit a hospital, may wait for hours at an emergency room, and may be examined by an inexperienced, overworked, or exhausted physician. Patients needing non-emergency care must call for an appointment during business hours and may wait on hold for an extended period. Changing an appointment may result in additional delay. Fees for health care are set unilaterally by the provider and are rarely negotiable. Health care providers make large capital investments and may experience swings in patient load that result in productive capacity being underutilized for extended periods. Providers cannot easily shift patient load once appointments have been committed. The inflexibility in appointment scheduling results in frustration for patients and uneven utilization of capital and human resources for health care providers contributing to a higher overall cost of health care to all.

SUMMARY

In an embodiment, a health clinic broker system is provided. The system comprises at least one computer system and a health clinic broker application that, when executed on the at least one computer system, receives a plurality of health care service requests containing information about a health care need, at least some of the requests seeking to set an appointment for health care. The system also receives a plurality of health care service offerings and provides at least one recommendation for the appointment for health care based on matching the health care service offerings with the health care service request.

In another embodiment, an automated method of setting of appointments for health care services is provided. The method comprises a computer receiving a health care service request, the health care service request including one or more of a description of symptoms, an urgency of need for care, a preferred appointment time, a preferred appointment date, and a preferred appointment location. The method also comprises the computer identifying candidate health care service appointments based on searching a database of health care service offerings using a location filter and the preferences received. The method also comprises the computer communicating appointment choices for health care service offerings, the computer receiving a choice of appointment, and the computer confirming the choice of appointment.

In another embodiment, a method of automatically scheduling delivery of health care services is provided. The method comprises an application monitoring a plurality of health care resources across time slots and facilities, the application executing on a computer system and the application identifying an opportunity to change a schedule of a health care service appointment to more efficiently use the health care resources. The method also comprises the application determining an incentive to tender as an inducement to change the schedule of the appointment, and the value of the incentive related to the benefit presented by the opportunity to change the schedule of the appointment. The method also comprises the application communicating the incentive to change the schedule of the health care service appointment based on load balancing across time slots and facilities.

These and other features will be more clearly understood from the following detailed description taken in conjunction with the accompanying drawings and claims.

BRIEF DESCRIPTION OF THE DRAWINGS

For a more complete understanding of the present disclosure, reference is now made to the following brief description, taken in connection with the accompanying drawings and detailed description, wherein like reference numerals represent like parts.

FIG. 6 is a block diagram of a mobile device according to an embodiment of the disclosure.

FIG. 7 is a block diagram of a software configuration for a mobile device according to an embodiment of the disclosure.

DETAILED DESCRIPTION

It should be understood at the outset that although illustrative implementations of one or more embodiments are illustrated below, the disclosed systems and methods may be implemented using any number of techniques, whether currently known or in existence. The disclosure should in no way be limited to the illustrative implementations, drawings, and techniques illustrated below, but may be modified within the scope of the appended claims along with their full scope of equivalents.

Several embodiments of a health clinic broker system permit a party in need of medical care to submit a request for an appointment and specify preferences including time, date, and location of appointment. The requesting party in reply may receive several alternative appointment choices, at least one of which may fit their needs better than could be achieved using a conventional method of requesting an appointment. The system consults databases of health care service provider offerings which include health care services available, clinic locations, physician gender, and available appointment times and dates. The system searches the databases for available appointments and selects appointments that most closely match the request received. The system may return several alternative appointment offerings to the requester. The requester reviews the list of available appointments, considers how each alternative matches with their medical condition and appointment preferences, and decides which appointment best meets their needs. The requester communicates their choice to the system which books the appointment with the chosen provider of health care services. The system confirms the appointment with the requester and the provider. In embodiments, the system may have access to the requester's health insurance information which may permit the system to make a more comprehensive and targeted search through its network of health care service providers and discover health care service alternatives and appointment choices even better suiting the requester's medical and financial situation.

Embodiments of the present system provide some market interaction between requesters and providers of health care services. Requesters are empowered to demand choice from providers, and providers are given the flexibility to offer alternatives and make adjustments to their offerings in accordance with the discipline demanded by market interaction. The system matches requests with offerings and gives alternatives to requestors. The system also gives providers the power to offer incentives to requesters to make changes in previously booked appointments when a provider encounters an overbooked situation in its scheduling, wishes to balance its patient load across its facilities, or faces an emergency requiring change in patient scheduling to provide critical care.

Figure 1:
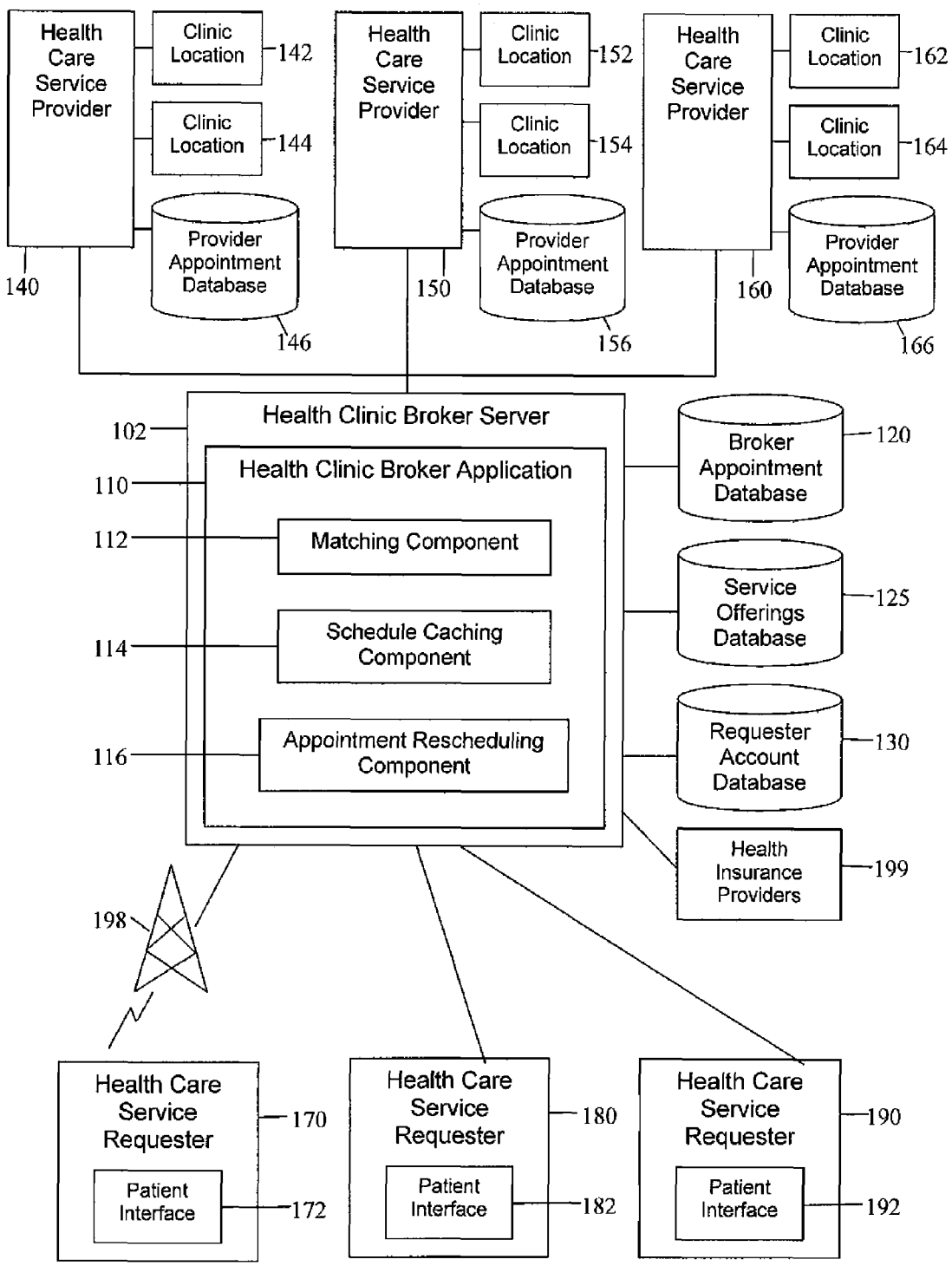
FIG. 1 is a block diagram of a system according to an embodiment of the disclosure.

Turning to FIG. 1, a health clinic broker system 100 is described. The system comprises a health clinic broker server 102, a health clinic broker application 110, a broker appointment database 120, a service offerings database 125, a requester account database 130, a first health care service provider 140, a first health care service requester 170, a wireless base station 198, and health insurance providers 199. In an embodiment, the system 100 further comprises a plurality of health care service providers including at least a second health care service provider 150 and a third health care service provider 160. In an embodiment, the system 100 further comprises a plurality of health care service requesters including at least a second health care service requester 180 and a third health care service requester 190. The system 100 also comprises provider appointment databases 146, 156, 166 that are components of the first health care service provider 140, second health care service provider 150, and third health care service provider 160, respectively.

While the first health care service provider 140, second health care service provider 150, third health care service provider 160, first health care service requester 170, second health care service requester 180, third health care service requester 190, and health insurance providers 199 are depicted in FIG. 1 as directly connected to the health clinic broker server 102, those components may communicate with the health clinic broker server 102 via a network connection. The network may be any communication network including a public data network (PDN), a public switched telephone network (PSTN), a private network, and/or a combination thereof.

The health clinic broker server 102 may be any general purpose computer system, as discussed in greater detail hereinafter. The health clinic broker server 102 may comprise one computer or a plurality of computers, for example a server farm wherein many server computers cooperate to share a processing load. The health clinic broker server 102 may comprise a plurality of computers which are located at different places, for example to provide geographical diversity and increased service reliability. The health clinic broker server 102 executes one or more applications that provide services to one or more of the health care service requesters 170, 180, 190 and health care service providers 140, 150, 160 including hosting of a health clinic broker application 110.

The health clinic broker application 110 resides on the health clinic broker server 102, receives health care service requests from the health care service requesters 170, 180, 190, and consults the broker appointment database 120 and the provider appointment databases 146, 156, 166. The health clinic broker application 110 comprises a matching component 112 which attempts to match the health care service request with one or more available appointments found while searching the broker appointment database 120 and the provider appointment databases 146, 156, 166. In an embodiment, the health clinic broker application 110 may include a schedule caching component 114 which receives appointment schedule updates from the provider appointment database 146, 156, 166. In an embodiment, the schedule caching component 114 synchronizes the appointment schedule updates received from the provider appointment database 146, 156, 166 with the appointment schedules maintained on the broker appointment database 120. The health clinic broker application 110 also includes an appointment rescheduling component 116 which searches the broker appointment database 120 and/or the provider appointment database 146, 156, 166 for overbooking and other situations that may call for rescheduling a confirmed appointment. The appointment rescheduling component 116 identifies instances of the health care service requester 170, 180, 190 holding confirmed appointments that represent candidates for rescheduling. The appointment rescheduling component 116 manages interactions with the health care service requester 170, 180, 190 and health care service provider 140, 150, 160 regarding proposed changes in appointment schedules and negotiates any changes in terms necessary to secure agreement to an appointment change by the health care service requester 170, 180, 190 including offering incentives to the health care service requester 170, 180, 190.

While the health clinic broker application 110 has been depicted as residing on the health clinic broker server 102, in an embodiment, components of the health clinic broker application 110 may reside on the servers or elsewhere within the information technology infrastructures of the health care service providers 140, 150, 160. When health care service requesters 170, 180, 190 need to communicate with the system 100 to interact about the possibility of changing an appointment and negotiating the terms of the change, the appointment rescheduling component 116, which is depicted as residing on the health clinic broker server 102, may delegate the authority to change appointments and negotiate pricing to software components that reside on the health care service providers 140, 150, 160 and have functionality similar to the appointment rescheduling component 116. Locating some of the functionality of the health clinic broker application 110 within the health care service providers 140, 150, 160 may provide processing efficiencies, in particular given the last-minute or immediate nature of negotiating a change of an imminent appointment and accompanying terms.

The broker appointment database 120 stores and makes information available to the health clinic broker server 102 and possibly other server computers that may execute applications unrelated to the system 100. The broker appointment database 120 contains a copy of the appointment schedules for the health care service providers 140, 150, 160. In an embodiment, the broker appointment database 120 may contain replica copies of the provider appointment databases 146, 156, 166 which are controlled by the health care service providers 140, 150, 160. In the embodiment, the broker appointment database 120 periodically receives updates from the provider appointment databases 146, 156, 166. The broker appointment database 120 may be implemented in a variety of manners known to those skilled in the art, including as a relational database, as an object-oriented database or according to some other data storage/access principles.

The service offerings database 125 retains information on program and service offerings made available by the health care service providers 140, 150, 160 for use by the health care service requesters 170, 180, 190. The health clinic broker application 110 may draw upon information in the service offerings database 125 in an effort to fulfill a health care service request submitted by one or more of the health care service requesters 170, 180, 190. The service offerings database 125 may be implemented in a variety of manners known to those skilled in the art, including as a relational database, as an object-oriented database or according to some other data storage/access principles.

The requester account database 130 stores and makes information available to the health clinic broker application 110 and possibly other server computers that may execute applications unrelated to the system 100. The requester account database 130 stores client records of the health care service requester 170, 180, 190 including account information related to a contractual relationship or other association that the health care service requester 170, 180, 190 may have with the health clinic broker application 110. The requester account database 130 may also contain information about the time, location, and physician gender preferences for a particular health care service requester 170, 180, 190. The requester account database 130 may also contain historical information about the willingness, inclination or propensity of a health care service requester 170, 180, 190 to change a previously booked appointment and the types of incentives historically used, if any, to induce the health care service requester 170, 180, 190 to accept an appointment change. The requester account database 130 may contain additional information about a particular health care service requester 170, 180, 190 including the preferred method of payment, a credit score, and patient status, including information about whether the requester is established or first-time. The requester account database 130 may be implemented in a variety of manners known to those skilled in the art, including as a relational database, as an object-oriented database or according to some other data storage/access principles.

The health care service provider 140, 150, 160 is one of a physician in private practice, two or more physicians in practice as a partnership or professional corporation, a hospital, an independent retail clinic or retail clinic associated with a conventional health care provider, or other entity providing health care services. Descriptions of the interactions of the health care service provider 140 may be taken as representative of the health care service providers 150, 160. The health care service provider 140 may conduct operations at more than one clinic location 142, 144 and operates a provider appointment database 146 in which appointments are booked. In an embodiment, the provider appointment database 146 is the authoritative repository of appointment information for the health care service provider 140. Appointment information in the provider appointment database 146 may be pushed to the broker appointment database 120 or pulled by the broker appointment database 120 from the provider appointment database 146. Descriptions of the operations of the health care service provider 140 at its clinic locations 142, 144 may be taken as representative of the operations of the health care service provider 150 at its clinic locations 152, 154 and the operations of the health care service provider 160 at its clinic locations 162, 164.

The health care service requester 170, 180, 190 is a device operated by a patient or other party in need of health care services including an appointment for medical care. The health care service requester 170, 180, 190 may be one of a mobile telephone, personal digital assistant (PDA), desktop telephone, laptop computer, tablet computer, desktop computer, or other electronic device with the capacity to communicate with the health clinic broker server 102. Descriptions of the interactions of the health care service requester 170 may be taken as representative of the health care service requester 180, 190. The health care service requester 170 comprises a patient interface 172 that the party operating the health care service requester 170 uses to enter information associated with initiating a health care service request, receiving a response from the health clinic broker application 110 containing available appointment alternatives, and submitting a choice of an appointment. The patient interface 172 is also used to communicate with the appointment rescheduling component 116 should a change to a previously booked appointment become a possibility for any reason.

The wireless base station 198 may be any of a cellular wireless base station, for example a Code Division Multiple Access (CDMA), Global System for Mobile Communications (GSM), and/or Universal Mobile Communications System (UMTS) cellular wireless base station; a World-wide Interoperable Microwave Access (WiMAX) base station; a WiFi access point; or other wireless access device. In an embodiment, the wireless base station 198 may be a femtocell. A femtocell, also known as an access point base station, may be a small cellular base station. The wireless base station 198 is in communication with the health clinic broker server 102, for example via wired communication links.

Health insurance providers 199 comprise one or more providers of health insurance coverage contracted for by patient(s) associated with the health care service requester 170. The health clinic broker application 110 may contact the health insurance providers 199 to verify coverage information for patient(s) associated with the health care service requester 170. The health clinic broker application 110 may contain functionality allowing it to submit health insurance claims to the health insurance providers 199 on behalf of the health care service requester 170 and the health care service provider 140 and receive and forward reimbursements and other payments to the various parties in the system 100.

Figure 2:
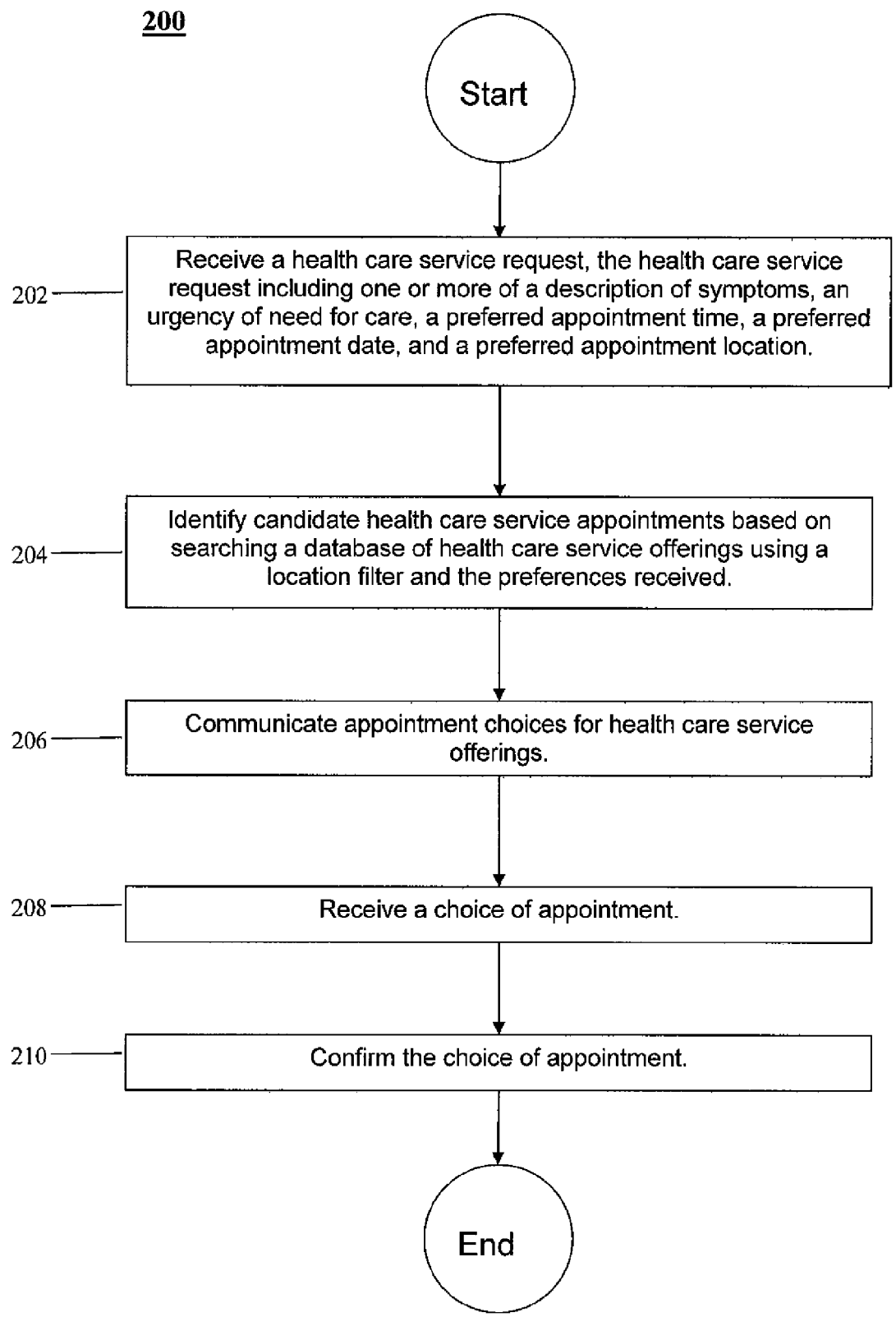
FIG. 2 is a flowchart illustrating a method according to an embodiment of the disclosure.

Turning now to FIG. 2, a method 200 of setting appointments is described. Beginning at block 202, the health clinic broker application 110 receives a health care service request from the health care service requester 170. The health care service request may include one or more of a description of the symptoms experienced, an urgency of need for care, a preferred appointment time, a preferred appointment date, a preferred appointment location, and a physician gender. The health care service request may also include a description of insurance coverage and a payment method. The health care service requester 170 may make additional specifications in its request including stipulating that the patient's health insurance is accepted by a provider or asking if a provider will make concessions such as waiving or reducing a co-payment. The health care service requester 170 may also mandate that a clinic or other provider be located within a certain radius from the health care service requester 170 and request that the patient not be subjected to waiting time after arrival. The health care service request may also include insurance coverage information for the patient associated with the health care service requester 170 and a method of payment for any services not covered by health insurance.

The health care service requester 170 may submit its health care service request to the health clinic broker application 110 and conduct subsequent interaction with the health clinic broker application 110 using one of a variety of methods comprising voice-activated or push button interaction on a mobile or desktop telephone, push-to-talk on a mobile phone, electronic mail which may use the simple mail transport protocol, or a web browser interface which may use the hypertext transfer protocol.

At block 204, the matching component 112 identifies candidate health care service appointments based on searching a database of health care service offerings using a location filter and the preferences received in the health care service request. The matching component 112 maps the user symptoms information to available clinic resources based on the most likely treatment plan for the symptoms reported by the health care service requester 170. The matching component 112 searches databases for the health care service provider 140 capable of meeting the needs of the health care service requester 170 given the symptoms reported, the preferences submitted, and patient load considerations across health care service providers during the period of time estimated for the care needed by the health care service requester 170.

In an embodiment, the matching component 112 promotes performing a pre-diagnosis interaction with the health care service requester 170 when the health care service requester 170 makes its initial contacts with the health clinic broker application 110. The matching component 112 may query the patient on specific symptoms experienced, duration of the symptoms, trends in symptoms experienced, and acuity of symptoms. In an embodiment, the matching component 112 may analyze the responses provided by health care service requester 170, take consideration of the combination of presented symptoms, apply weights to the responses, and consult diagnostic databases and computer applications not specifically described as components of the system 100. In an embodiment, the pre-diagnosis function of the matching component 112 may be a separate component (not shown in FIG. 1) and may communicate with a diagnostic database (not shown in FIG. 1) comprising diagnostic information, for example, but not limited to, associations between symptoms and medical conditions and/or treatment protocols. In an embodiment, the matching component 112 may identify an emergency situation when the health care service requester 170 did not previously perceive an emergency and take action to provide urgently needed care promptly. In an embodiment, the matching component 112 maps reported symptoms to urgency, qualifications needed by health care personnel, diagnostic and treatment equipment needed at a facility, estimated time for examination and treatment before searching databases of health care service offerings for available appointments. In an embodiment, the results of the pre-diagnosis is employed by the matching component 112 in identifying available appointments for the health care service requester 170.

In some embodiments, the matching component 112 searches for available appointments in the broker appointment database 120. The broker appointment database 120 may be directly connected or otherwise local to the health clinic broker server 102 and more easily accessible to the health clinic broker application 110 than the provider appointment database 146 that is local to the health clinic service provider 140 and may be part of the patient management system of the health care service provider 140. The broker appointment database 120, as primary source of appointment information to the health clinic broker application 110 but not the authoritative source, will synchronize with the provider appointment database 146 using the schedule caching component 114 such that the appointment records in the broker appointment database 120 closely or exactly match the authoritative appointment records in the provider appointment database 146. The schedule caching component 114 may cause the broker appointment database 120 and the provider appointment database 146 to replicate or synchronize their records using any one of various methods known to those skilled in the art. The broker appointment database 120 may initiate synchronization with the provider appointment database 146 by polling at specified time intervals or whenever a change is made to either database. The provider appointment database 146 may periodically furnish only its incremental changes, for example deltas, since the previous update or replication with the broker appointment database 120, or the provider appointment database 146 may fully replicate with the broker appointment database 120 in a manner known to those skilled in the art. In other embodiments, the matching component 112 may directly access the provider appointment database 146 for information on appointment availability.

Continuing at block 204, once the matching component 112 has used a location filter to determine one or more of a health care service provider 140 that fits the location preference specified by the health care service requester 170 and determines that the identified health care service provider 140 is able to provide a treatment plan for the medical condition reported by the health care service requester 170, the matching component 112 then searches on the other preferences submitted by the health care service requester 170. The matching component 112 considers the time and date preferences and any other preferences or requests such as a request for a physician gender or for waiver or reduction of co-payment. The matching component 112 considers the symptoms described and all of the preferences specified in the health care service request and generates candidate health care service appointments that meet the maximum number of preferences specified given the results of applying the location filter. The matching component 112, in addition to consulting the provider appointment database 146, the broker appointment database 120, and/or additional appointment databases for available appointment slots, may submit appointment requests containing special preference parameters requiring deliberation by the health care service provider 140 and a specific bid reply by the health care service provider 140. The specific bid reply may contain parameters that are unique to that bid reply. The health care service provider 140 may also make available a limited quantity of standing appointment offers containing specialized features that are available only to requesters with specific preferences that closely or exactly match the specialized features. In an embodiment, a health care service provider 140 may actively seek to serve health care service requesters 170 reporting specific symptoms that are related to clinical trials that the health care service provider 140 may currently be conducting and/or that are likely to call for treatment using newly acquired equipment. A health care service provider 140 may structure its service offerings including pricing in accordance with its business needs and diagnostic and treatment strengths to attract health care service requesters 170 with certain symptoms, conditions, and needs.

In some embodiments, the health clinic broker application 110 examines patient activity and load across the health care service provider 140 and may present a selection of appointment offerings such that the health care service requester 170 is inclined to choose an appointment that assists in the process of balancing patient load. The health clinic broker application 110 seeks to balance patient load and assist the health care service provider 140 efficiently use its facilities and human resources as well as assist patients with finding care. If the health clinic broker application 110, in assembling appointment alternatives for submission back to the health care service requester 170, identifies one or more opportunities to better achieve balancing of patient load by altering the choices offered to the health care service requester 170, it may do so. The health care service provider 140 that experiences imbalances in patient load or uneven utilization of its facilities may decide to offer incentives that the matching component 112 may use in its dealings with the health care service requester 170 to influence the health care service requester 170 to accept an appointment offering that helps the health care service provider 140 achieve improved utilization.

The matching component 112, independent of or not independent of a specific health care service request, may scan the provider appointment database 146, the broker appointment database 120, and/or additional appointment databases to detect imbalances in patient load, over- or underutilization of provider facilities, or other indications that prospective changes in appointment scheduling practices may provide financial or operational benefit to the health care service provider 140. The matching component 112 has access to the pricing schedules of the health care service provider 140. In scanning current appointment databases and historical appointment activity, the matching component 112 may also discover opportunities for prospective appointment schedule and pricing adjustments that may improve utilization and revenue for the health care service provider 140 while maintaining an acceptable level of care and service to the health care service requester 170.

In an embodiment, a health care service requester 170 may have scheduling needs or other preferences such that it is willing to pay a premium amount, for example 20% more than the standard fee, for an immediate appointment in a time slot currently held by health care service requester 180. In the example, if the health care service requester 180 is willing to release the appointment and take a different appointment by accepting an offer from the health care service provider 140 of a 15% discount from the standard fee, the health care service provider 140 then realizes a double benefit of increasing revenue by the 5% differential and also booking two appointments (the immediate appointment paying a premium as well as the rescheduled appointment offered a discount) instead of just one. The health clinic broker application 110 provides functionality to repeatedly view the types of initial contacts it is receiving from health care service requesters 170, scan the appointment databases for currently booked appointments, and review any historic patterns of behavior by both health care service requesters 170 with existing appointments and health care service requesters 170 seeking appointments to identify scheduling adjustments that may be made that result in improved revenue for a health care service provider 140 or assist a health care service provider 140 in utilizing its facilities more advantageously while also providing an acceptable level of service and care to the health care service requester 170.

At block 206, the matching component 112 communicates appointment choices for health care service offerings to the health care service requester 170. In an embodiment, the appointment choices may be reserved and held available for the health care service requester 170 for a stated amount of time with availability of the appointment slots guaranteed until the stated deadline. In other embodiments, appointment slots at the health care service provider 140 may be made available on a first-come-first-served basis. In the embodiment, time is of the essence for the health care service requester 170 as appointment slots made available to the health care service requester 170 may have also concurrently been made available to the health care service requester 180, 190. The party that is the first to choose an available appointment slot is awarded it. In either embodiment presented, the matching component 112 submits to the health care service requester 170 appointment alternatives based on the symptoms indicated and preferences expressed by the health care service requester 170.

At block 208, the health clinic broker application 110 receives a choice of appointment from the health care service requester 170. The health clinic broker application 110 checks the broker appointment database 120 and/or the provider appointment database 146, confirms that the chosen appointment is still available, and books the appointment. The appointment is committed to the provider appointment database 146 and the broker appointment database 120. At block 210, the health clinic broker application 110 confirms the choice of appointment by sending an electronic mail, SMS text message, or other notification to the health care service requester 170 and the health care service provider 140.

Figure 3:
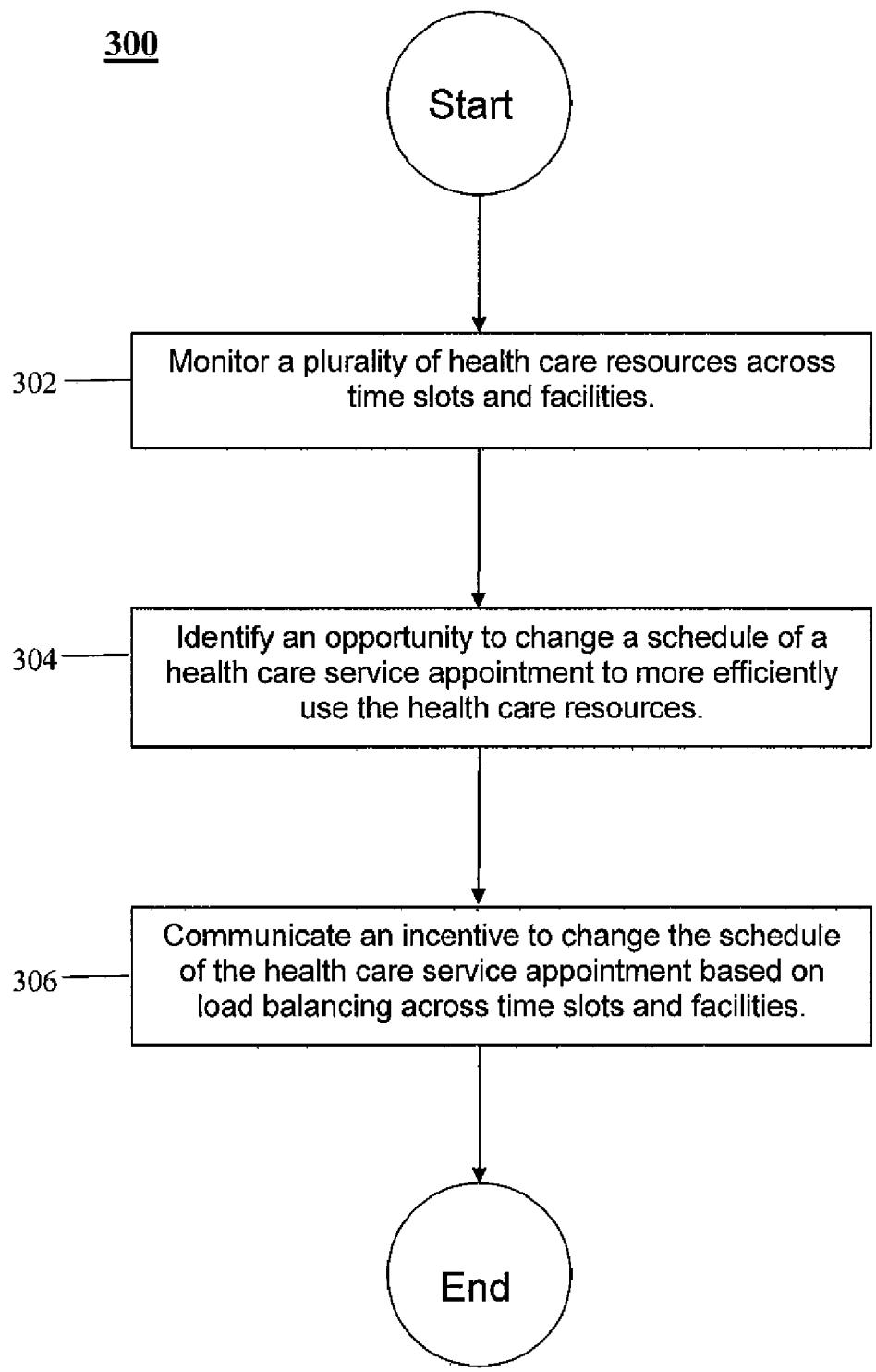
FIG. 3 is another flowchart illustrating a method according to an embodiment of the disclosure.

Turning now to FIG. 3, a method 300 of scheduling delivery of health care services is described. Beginning at block 302, the health clinic broker application 110 monitors a plurality of health care resources across time slots and facilities. Similar to its review in the method 200 of historical appointment activity to prospectively change scheduling practices for new appointment requests to achieve long-term operational and financial improvements, the health clinic broker application 110 may also seek short-term benefit by examining existing schedules of previously booked appointments to search for overbooked situations or abnormal over- or underutilizations of facilities. Such anomalies may be alleviated by inducing the health care service requester 170 with booked appointments to accept changes to their appointments, thus better aligning appointments with facilities. At block 302, the health clinic broker application 110 scans the provider appointment database 146, the broker appointment database 120, and/or additional appointment databases to discover appointment overbooking and facility utilization imbalances that may be alleviated by inducing parties holding confirmed appointments to accept changes. The health clinic broker application 110 in its process of scanning databases and facilities may also discover opportunities to generate improved revenue for the health care service provider 140 by inducing the health care service requester 170 with booked appointments to accept appointment changes. The method 300 may allow improvements in provider productivity or provider revenue by shifting previously booked appointments.

At block 304, the health clinic broker application 110 searches for overcommitted appointment booking situations in which consecutive appointment slots may be booked with appointments for illness diagnoses that will likely result in physician visit time exceeding the allotted time for scheduled appointment slots. The health care service provider 140 may make innocent judgment errors in allotting time slots for certain diagnoses or may misunderstand or misjudge the seriousness or urgency of the condition of one or more of the health care service requester 170. In other instances, the health care service requester 170 may be the party which misjudges or poorly communicates the seriousness or urgency of a medical condition. Regardless of fault, misunderstandings may occur when symptoms, speculations about diagnoses, and other health matters are communicated. Situations may also arise when a physician committed to one or more appointments is called away on an emergency and the appointments to which that physician was committed must be covered by other physicians at the same location, another location of the same clinic, or at another clinic altogether. Rescheduling booked appointments may be necessary as other physicians may not be available to cover for the physician called away on the emergency.

Genuine emergencies occasionally arise which may overwhelm the ability of the health care service provider 140 to absorb an unexpected patient load. A sudden increase in motor vehicle accidents caused by inclement weather, a natural disaster, an airplane crash, an outbreak of illness or violence at a school or workplace, a serious explosion or fire, or a terrorist attack are examples of events which may create a sudden and serious imbalance of patient load for a health care service provider 140. The need may suddenly arise to reschedule previously booked appointments or move previously booked appointments to a different health care service provider 140.

Situations will also arise in which facilities are not overbooked and no emergency has occurred or in danger of occurring but the health clinic broker application 110 in its scanning of databases identifies scheduling of booked appointments in which some facilities are being significantly overused and other facilities are nearly idle for extended periods. Such imbalances of facility utilization may be accompanied by uneven utilization of human resources as medical and administrative personnel in one case are overworked with morale suffering and personnel in the other case are being paid but are underutilized. Equipment in use at the health care service provider 140 may be subject to lease agreements with penalty usage charges incurred with excessive usage. For the health care service provider 140 with multiple locations, it may be both in its economic interest as well as in the interest of quality of patient care to evenly distribute patient load across facilities and in accordance with physician specialties.

Whether an imbalance of patient appointment bookings calling for rescheduling or shifting arises from accidental or unintentional overbooking, an emergency or possibility of emergency, or arises naturally from normal request activity by the health care service requester 170, the appointment rescheduling component 116 commences the process of examining databases of booked appointments to identify candidates for rescheduling. The appointment rescheduling component 116 reviews the requester account database 130 for information on the health care service requester 170 to determine the inclination or willingness of parties with previously booked appointments to accept changes in appointment time, date, location, physician preference or other preference item.

The appointment rescheduling component 116 seeks to address the overbooked condition, emergency, or other booking imbalance with the minimum of shifting or rescheduling of previously booked patient appointments. Quality of customer service with a minimum of inconvenience to customers is sought and the appointment rescheduling component scans appointment databases and determines what scheduling changes are necessary to alleviate the anomalous situation. The appointment rescheduling component 116 in its review of account history contained in the requester account database 130, may identify instances of the health care service requester 170 that have in the past responded positively to offers of incentives to accept a rescheduling of a booked appointment. Such incentives may include a waiver of a co-payment, the offering of a coupon, or other concession.

In an embodiment, the health care service provider 140 may be one of a private, for-profit clinic, in business as either an independent entity or as part of a chain organization, and may provide service to patients on both a walk-in and appointment basis. Such a clinic may be fully booked with appointments but experience an unexpected number of walk-in patients. Instead of turning away the walk-in patients or cause long wait times, the clinic may send messages to the health care service requester 170 holding confirmed appointments and ask the health care service requester 170 if the health care service requester 170 would be willing to come at a different time or go to a different location. The clinic may offer an incentive to the health care service requester 170 as an inducement to secure its agreement to an appointment rescheduling and/or location change. The clinic alternatively may wish to honor its appointment commitments to parties holding confirmed appointments and offer the unexpected walk-in patients incentives to return to the same clinic at a later time, travel to another branch location of the same clinic, or go to a nearby competitor clinic.

The clinic may also choose to selectively provide some holders of confirmed appointments and walk-in patients with incentives to delay their care while honoring their appointment commitments to other patients and immediately serving other walk-in patients. Such decisions by the health care service provider 140 may be impacted by availability of physician specialties at a clinic or during periods of time, the urgency of medical conditions reported by walk-in patients, or the willingness or flexibility of walk-in patients or parties with confirmed appointments to accept changes in delivery of their care. The appointment rescheduling component 116 examines the provider appointment database 146 and the broker appointment database 120 to identify opportunities to better balance patient load which may lead to reduced cost of servicing to the health care service requester 170 as well as better patient care and satisfaction.

The appointment rescheduling component 116 in its scanning of the provider appointment database 146 and the broker appointment database 120 may also discover situations in which changing of one or more previously booked appointment for health care may cause a purely financial benefit to the health care service provider 140 in which there is no overbooking or facility usage consideration. In embodiments, providing selective incentives to the health care service requester 170 to accept changes in appointment scheduling may permit the health care service provider 140 to employ fewer physicians or hourly personnel during a period of time or incur a lower fixed operating cost. Insurance reimbursements may be more favorable with an adjusted balance of patient appointments, for example. At block 304, the appointment rescheduling component 116, scans one or more databases of previously booked appointments to identify opportunities for schedule changes to more efficiently use the resources of the health care service provider 140, resolve an overbooking situation, meet the critical care demands presented by an emergency situation, assist with an unexpected increase in walk-in patients at a clinic, or take advantage of an opportunity for financial gain presented by circumstances.

At block 306, the appointment rescheduling component 116 communicates an incentive to change the schedule of the health care service appointment based on load balancing across time slots and facilities or based on achieving one of the other benefits of this action previously described. Depending on the response of the health care service requester 170 to receiving the request for rescheduling of appointment and accompanying incentive, the appointment rescheduling component 116 may need to adjust an incentive including increasing the value of an incentive or changing an incentive. The appointment rescheduling component 116 may alternatively need to abandon efforts to cause the health care service requester 170 to agree to the rescheduling of its appointment. The health care service requester 170 may also respond affirmatively to the incentive tendered by the appointment rescheduling component 116 and accept its offer to reschedule its appointment. In this instance, the appointment rescheduling appointment 116 would need to rebook the appointment with the broker appointment database 120 and confirm the changed appointment with the health care service requester 170 and the health care service provider 140 with whom the rescheduled appointment is being booked.

The health clinic broker application 110 may in its scanning of the provider appointment database 146, the broker appointment database 120, and/or additional appointment databases, discover situations in which it may be appropriate to provide an incentive to the health care service provider 140 to make changes in its scheduling of appointments, allotments of appointment time for reported diagnoses, or valuations or weightings given to preferences provided by the health care service requester 170. Such changes may be of a short term nature to overcome a temporary increase in requests for appointments by the health care service requester or may be of a longer term, structural nature, for example the opening of a large industrial facility near the health care service provider 140 that may necessitate a permanent expansion of hours to accommodate the large amount of expected activity.

Figure 4:
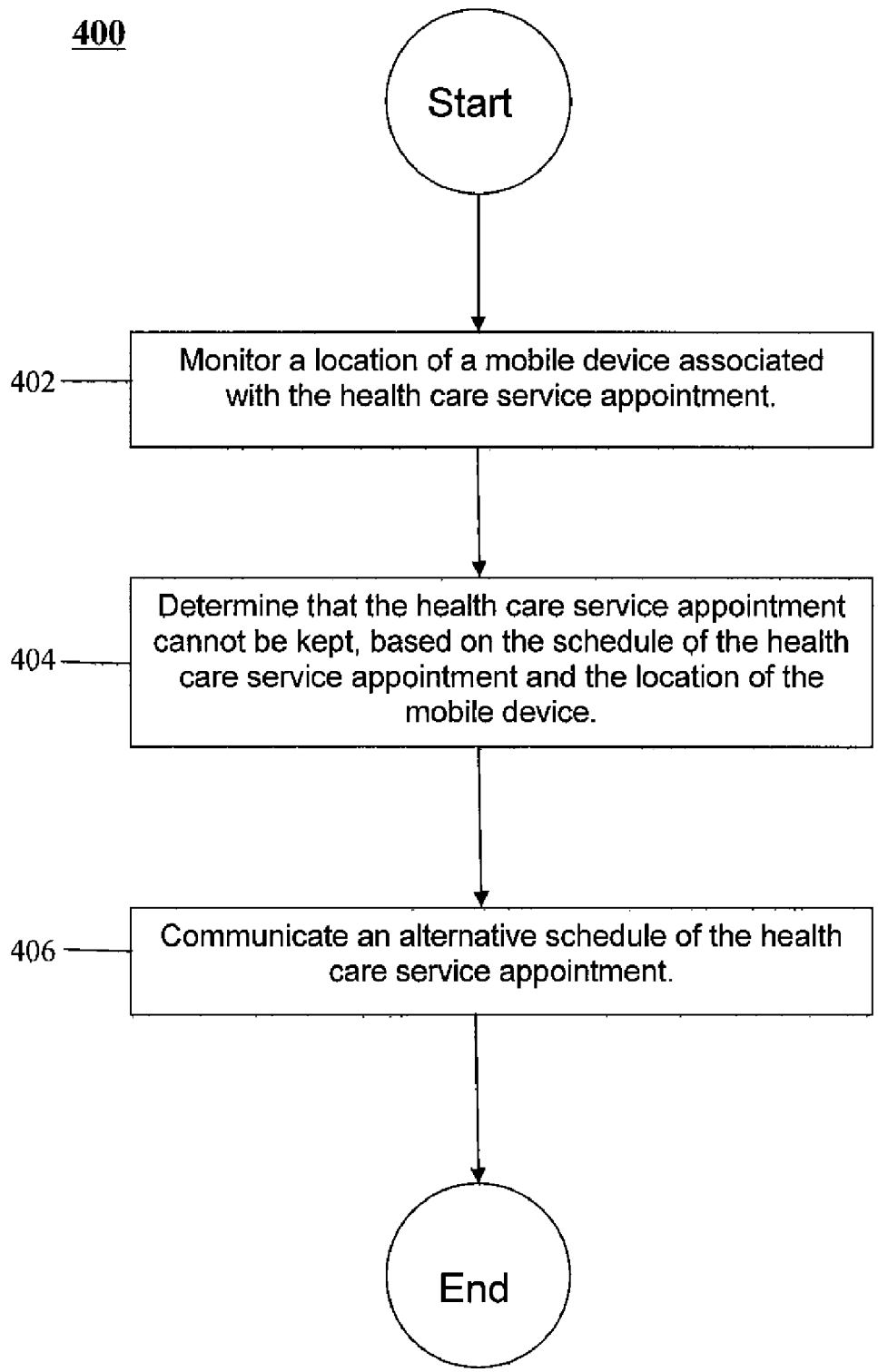
FIG. 4 is another flowchart illustrating a method according to an embodiment of the disclosure.

Turning now to FIG. 4, a method 400 for maintaining prompt compliance with scheduled health care service appointments is described. Beginning at block 402, the health clinic broker application 110 monitors the location of the health care service requester 170 in advance of the time of a confirmed appointment for the health care service requester 170 with the health care service provider 140. In an embodiment, the health care service requester 170 may carry a mobile phone, personal digital assistant, or other mobile device whose location may be reportable by the health care service requester 170 and/or discoverable by the health clinic broker application 110. The reporting of the location of the health care service requester 170 may be initiated by the health care service requester 170 generating a message containing its location coordinates or other location identifying information to the health clinic broker application 110. Alternatively, the health clinic broker application 110 may initiate discovery by transmitting signals that the health care service requester 170 may receive and reply to with a report of its present location. The health clinic broker application 110 may send one or more appointment reminders with adequate advance notice to the health care service requester 170 such that the health care service requester 170 is given ample time to travel to the health care service provider 140 and keep the prearranged appointment.

In an embodiment, the health clinic broker application 110 has access to external information sources permitting it to analyze current and historic automobile traffic activity in geographic areas surrounding health care service providers 140. The health clinic broker application 110 may also review the history of various health care service requesters 170 in traveling to specific health care service providers 140 at different times of day including their travel times in reaching the specific health care service providers 140 from various starting points. This information may be used by the health clinic broker application 110 in making determinations about the likelihood of one or more health care service requesters 170 of arriving promptly for appointments. The ability to make these determinations earlier and more accurately permits the health clinic broker application 110 to have wider field of choice in offering rescheduling alternatives to health care service requesters 170 and identifying revenue enhancement and facility utilization opportunities.

At block 404, the health clinic broker application 110 may determine from discovering the current location of the health care service requester 170 that the health care service requester 170 will not be able to keep an appointment. The health clinic broker application 110 may calculate the distance between the health care service requester 170 and the health care service provider 140 far enough in advance such that if the health clinic broker application 110 determines that the health care service requester 170 will be unable to keep its agreed appointment time with the health care service provider 140, the health clinic broker application 110 may have adequate time to fill the appointment slot with another health care service requester 170.

At block 406, the health clinic broker application 110 may communicate to the health care service requester 170 that is unable (or projected to be unable) to keep its appointment an alternative schedule of health care service appointments. The alternative schedule offered by the health clinic broker application 110 may include different times or potentially different locations more convenient to the current location of the health care service requester 170. For example, the health care service requester 170 may be offered an appointment at the same time but at a health care service provider 140 located closer to the current location of the health care service requester 170. The health care service requester 170 will review the new list of alternative appointments, communicate its choice back to the health clinic broker application 110 that will book and confirm the new appointment as described previously.

Figure 5:
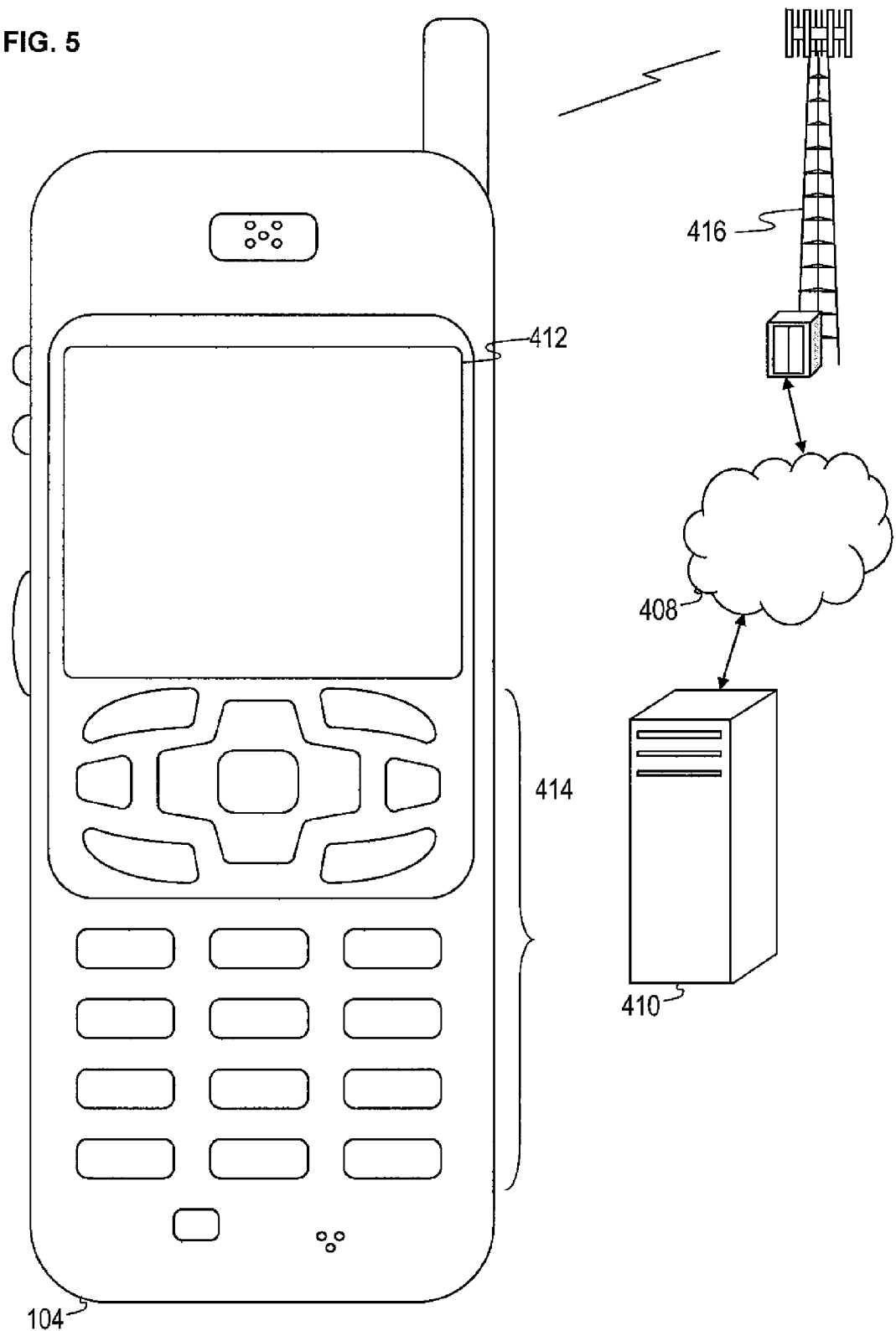
FIG. 5 is an illustration of a mobile device according to an embodiment of the disclosure.

FIG. 5 shows a wireless communications system including the handset 104. FIG. 5 depicts the handset 104, which is operable for implementing aspects of the present disclosure, but the present disclosure should not be limited to these implementations. Though illustrated as a mobile phone, the handset 104 may take various forms including a wireless handset, a pager, a personal digital assistant (PDA), a portable computer, a tablet computer, or a laptop computer. Many suitable handsets combine some or all of these functions. In some embodiments of the present disclosure, the handset 104 is not a general purpose computing device like a portable, laptop or tablet computer, but rather is a special-purpose communications device such as a mobile phone, wireless handset, pager, or PDA. The handset 104 may support specialized activities such as gaming, inventory control, job control, and/or task management functions, and so on.

The handset 104 includes a display 412 and a touch-sensitive surface or keys 414 for input by a user. The handset 104 may present options for the user to select, controls for the user to actuate, and/or cursors or other indicators for the user to direct. The handset 104 may further accept data entry from the user, including numbers to dial or various parameter values for configuring the operation of the handset. The handset 104 may further execute one or more software or firmware applications in response to user commands. These applications may configure the handset 104 to perform various customized functions in response to user interaction. Additionally, the handset 104 may be programmed and/or configured over-the-air, for example from a wireless base station, a wireless access point, or a peer handset 104.

The handset 104 may execute a web browser application which enables the display 412 to show a web page. The web page may be obtained via wireless communications with a cell tower 416, a wireless network access node, a peer handset 104 or any other wireless communication network or system. The cell tower 416 (or wireless network access node) is coupled to a wired network 408, such as the Internet. Via the wireless link and the wired network, the handset 104 has access to information on various servers, such as a server 410. The server 410 may provide content that may be shown on the display 412. Alternately, the handset 104 may access the cell tower 416 through a peer handset 104 acting as an intermediary, in a relay type or hop type of connection.

FIG. 6 shows a block diagram of the handset 104. While a variety of known components of handsets 104 are depicted, in an embodiment a subset of the listed components and/or additional components not listed may be included in the handset 104. The handset 104 includes a digital signal processor (DSP) 502 and a memory 504. As shown, the handset 104 may further include an antenna and front end unit 506, a radio frequency (RF) transceiver 508, an analog baseband processing unit 510, a microphone 512, an earpiece speaker 514, a headset port 516, an input/output interface 518, a removable memory card 520, a universal serial bus (USB) port 522, an infrared port 524, a vibrator 526, a keypad 528, a touch screen liquid crystal display (LCD) with a touch sensitive surface 530, a touch screen/LCD controller 532, a charge-coupled device (CCD) camera 534, a camera controller 536, and a global positioning system (GPS) sensor 538. In an embodiment, the handset 104 may include another kind of display that does not provide a touch sensitive screen. In an embodiment, the DSP 502 may communicate directly with the memory 504 without passing through the input/output interface 518.

The DSP 502 or some other form of controller or central processing unit operates to control the various components of the handset 104 in accordance with embedded software or firmware stored in memory 504 or stored in memory contained within the DSP 502 itself. In addition to the embedded software or firmware, the DSP 502 may execute other applications stored in the memory 504 or made available via information carrier media such as portable data storage media like the removable memory card 520 or via wired or wireless network communications. The application software may comprise a compiled set of machine-readable instructions that configure the DSP 502 to provide the desired functionality, or the application software may be high-level software instructions to be processed by an interpreter or compiler to indirectly configure the DSP 502.

The antenna and front end unit 506 may be provided to convert between wireless signals and electrical signals, enabling the handset 104 to send and receive information from a cellular network or some other available wireless communications network or from a peer handset 104. In an embodiment, the antenna and front end unit 506 may include multiple antennas to support beam forming and/or multiple input multiple output (MIMO) operations. As is known to those skilled in the art, MIMO operations may provide spatial diversity which can be used to overcome difficult channel conditions and/or increase channel throughput. The antenna and front end unit 506 may include antenna tuning and/or impedance matching components, RF power amplifiers, and/ or low noise amplifiers.

The RF transceiver 508 provides frequency shifting, converting received RF signals to baseband and converting baseband transmit signals to RF. In some descriptions a radio transceiver or RF transceiver may be understood to include other signal processing functionality such as modulation/ demodulation, coding/decoding, interleaving/deinterleaving, spreading/despreading, inverse fast Fourier transforming (IFFT)/fast Fourier transforming (FFT), cyclic prefix appending/removal, and other signal processing functions. For the purposes of clarity, the description here separates the description of this signal processing from the RF and/or radio stage and conceptually allocates that signal processing to the analog baseband processing unit 510 and/or the DSP 502 or other central processing unit. In some embodiments, the RF transceiver 408, portions of the antenna and front end 506, and the analog baseband processing unit 510 may be combined in one or more processing units and/or application specific integrated circuits (ASICs).

The analog baseband processing unit 510 may provide various analog processing of inputs and outputs, for example analog processing of inputs from the microphone 512 and the headset port 516 and outputs to the earpiece speaker 514 and the headset port 516. To that end, the analog baseband processing unit 510 may have ports for connecting to the built-in microphone 512 and the earpiece speaker 514 that enable the handset 104 to be used as a cell phone. The analog baseband processing unit 510 may further include a port for connecting to a headset or other hands-free microphone and speaker configuration. The analog baseband processing unit 510 may provide digital-to-analog conversion in one signal direction and analog-to-digital conversion in the opposing signal direction. In some embodiments, at least some of the functionality of the analog baseband processing unit 510 may be provided by digital processing components, for example by the DSP 502 or by other central processing units.

The DSP 502 may perform modulation/demodulation, coding/decoding, interleaving/deinterleaving, spreading/despreading, inverse fast Fourier transforming (IFFT)/fast Fourier transforming (FFT), cyclic prefix appending/removal, and other signal processing functions associated with wireless communications. In an embodiment, for example in a code division multiple access (CDMA) technology application, for a transmitter function the DSP 502 may perform modulation, coding, interleaving, and spreading, and for a receiver function the DSP 502 may perform despreading, deinterleaving, decoding, and demodulation. In another embodiment, for example in an orthogonal frequency division multiplex access (OFDMA) technology application, for the transmitter function the DSP 502 may perform modulation, coding, interleaving, inverse fast Fourier transforming, and cyclic prefix appending, and for a receiver function the DSP 502 may perform cyclic prefix removal, fast Fourier transforming, deinterleaving, decoding, and demodulation. In other wireless technology applications, yet other signal processing functions and combinations of signal processing functions may be performed by the DSP 502.

The DSP 502 may communicate with a wireless network via the analog baseband processing unit 510. In some embodiments, the communication may provide Internet connectivity, enabling a user to gain access to content on the Internet and to send and receive e-mail or text messages. The input/output interface 518 interconnects the DSP 502 and various memories and interfaces. The memory 504 and the removable memory card 520 may provide software and data to configure the operation of the DSP 502. Among the interfaces may be the USB port 522 and the infrared port 524. The USB port 522 may enable the handset 104 to function as a peripheral device to exchange information with a personal computer or other computer system. The infrared port 524 and other optional ports such as a Bluetooth interface or an IEEE 802.11 compliant wireless interface may enable the handset 104 to communicate wirelessly with other nearby handsets and/or wireless base stations.

The input/output interface 518 may further connect the DSP 502 to the vibrator 526 that, when triggered, causes the handset 104 to vibrate. The vibrator 526 may serve as a mechanism for silently alerting the user to any of various events such as an incoming call, a new text message, and an appointment reminder.

The keypad 528 couples to the DSP 502 via the interface 518 to provide one mechanism for the user to make selections, enter information, and otherwise provide input to the handset 104. Another input mechanism may be the touch screen LCD 530, which may also display text and/or graphics to the user. The touch screen LCD controller 532 couples the DSP 502 to the touch screen LCD 530.

The CCD camera 534 enables the handset 104 to take digital pictures. The DSP 502 communicates with the CCD camera 534 via the camera controller 536. The GPS sensor 538 is coupled to the DSP 502 to decode global positioning system signals, thereby enabling the handset 104 to determine its position. In another embodiment, a camera operating according to a technology other than charge coupled device cameras may be employed. Various other peripherals may also be included to provide additional functions, e.g., radio and television reception.

FIG. 7 illustrates a software environment 602 that may be implemented by the DSP 502. The DSP 502 executes operating system drivers 604 that provide a platform from which the rest of the software operates. The operating system drivers 604 provide drivers for the handset hardware with standardized interfaces that are accessible to application software. The operating system drivers 604 include application management services ("AMS") 606 that transfer control between applications running on the handset 104. Also shown in FIG. 6 are a web browser application 608, a media player application 610, and JAVA applets 612. The web browser application 608 configures the handset 104 to operate as a web browser, allowing a user to enter information into forms and select links to retrieve and view web pages. The media player application 610 configures the handset 104 to retrieve and play audio or audiovisual media. The JAVA applets 612 configure the handset 104 to provide games, utilities, and other functionality. The patient interface 614 corresponds to the patient interface 172, 182, 192 described as components of the system 100.

Figure 8:
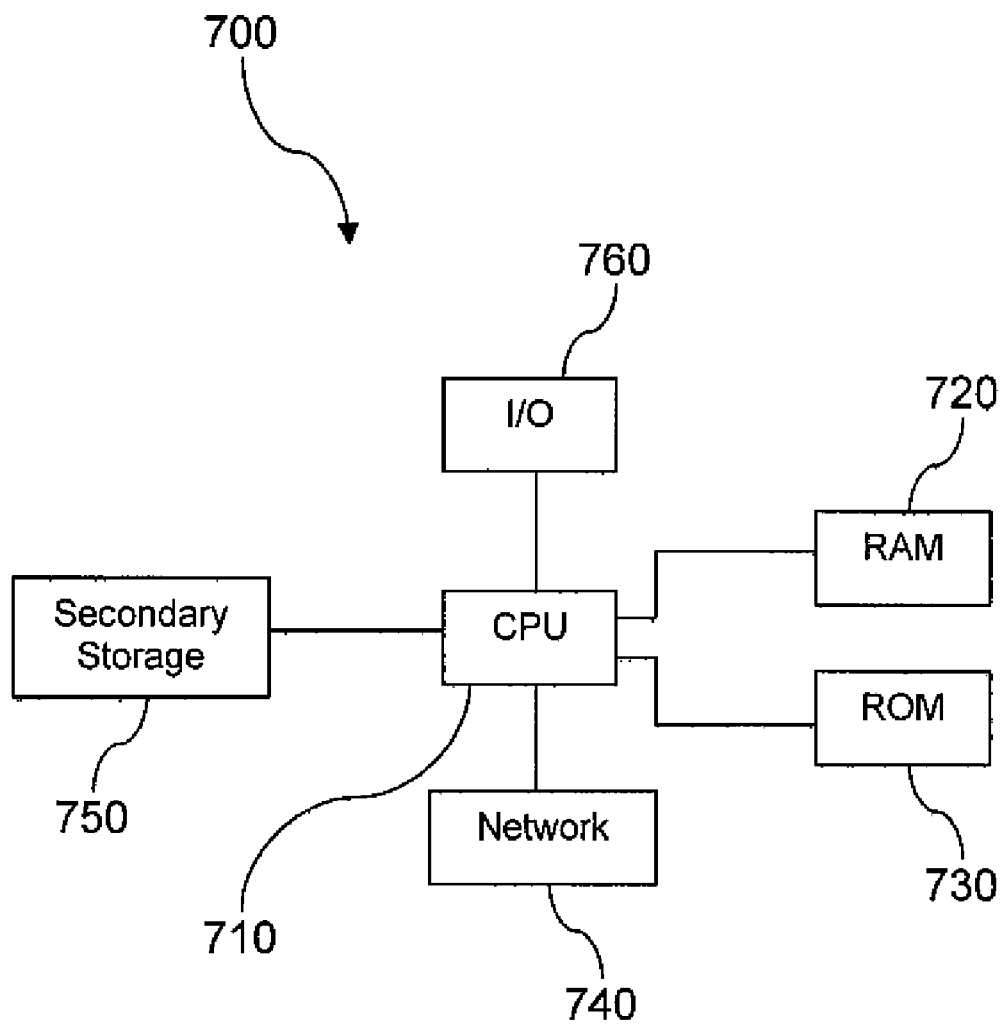
FIG. 8 illustrates an exemplary general purpose computer system suitable for implementing some aspects of the several embodiments of the disclosure.

Aspects of the system 100 described above may be implemented on any general-purpose computer with sufficient processing power, memory resources, and network throughput capability to handle the necessary workload placed upon it. FIG. 8 illustrates a typical, general-purpose computer system suitable for implementing one or more embodiments disclosed herein. The computer system 700 includes a processor 710 (which may be referred to as a central processor unit or CPU) that is in communication with memory devices including secondary storage 750, read only memory (ROM) 730, random access memory (RAM) 720, input/output (I/O) devices 760, and network connectivity devices 740. The processor may be implemented as one or more CPU chips.

The secondary storage 750 is typically comprised of one or more disk drives or tape drives and is used for non-volatile storage of data and as an over-flow data storage device if RAM 720 is not large enough to hold all working data. Secondary storage 750 may be used to store programs which are loaded into RAM 720 when such programs are selected for execution. The ROM 730 is used to store instructions and perhaps data which are read during program execution. ROM 730 is a non-volatile memory device which typically has a small memory capacity relative to the larger memory capacity of secondary storage. The RAM 720 is used to store volatile data and perhaps to store instructions. Access to both ROM 730 and RAM 720 is typically faster than to secondary storage 750.

I/O devices 760 may include printers, video monitors, liquid crystal displays (LCDs), touch screen displays, keyboards, keypads, switches, dials, mice, track balls, voice recognizers, card readers, paper tape readers, or other well-known input devices.

The network connectivity devices 740 may take the form of modems, modem banks, Ethernet cards, universal serial bus (USB) interface cards, serial interfaces, token ring cards, fiber distributed data interface (FDDI) cards, wireless local area network (WLAN) cards, radio transceiver cards such as code division multiple access (CDMA), global system for mobile communications (GSM), and/or worldwide interoperability for microwave access (WiMAX) radio transceiver cards, and other well-known network devices. These network connectivity devices 740 may enable the processor 740 to communicate with an Internet or one or more intranets. With such a network connection, it is contemplated that the processor 710 might receive information from the network, or might output information to the network in the course of performing the above-described method steps. Such information, which is often represented as a sequence of instructions to be executed using processor 710, may be received from and outputted to the network, for example, in the form of a computer data signal embodied in a carrier wave.

Such information, which may include data or instructions to be executed using processor 710 for example, may be received from and outputted to the network, for example, in the form of a computer data baseband signal or signal embodied in a carrier wave. The baseband signal or signal embodied in the carrier wave generated by the network connectivity devices 740 may propagate in or on the surface of electrical conductors, in coaxial cables, in waveguides, in optical media, for example optical fiber, or in the air or free space. The information contained in the baseband signal or signal embodied in the carrier wave may be ordered according to different sequences, as may be desirable for either processing or generating the information or transmitting or receiving the information. The baseband signal or signal embodied in the carrier wave, or other types of signals currently used or hereafter developed, referred to herein as the transmission medium, may be generated according to several methods well known to one skilled in the art.

The processor 710 executes instructions, codes, computer programs, scripts which it accesses from hard disk, floppy disk, optical disk (these various disk based systems may all be considered secondary storage 750), ROM 730, RAM 720, or the network connectivity devices 740. While only one processor 710 is shown, multiple processors may be present. Thus, while instructions may be discussed as executed by a processor, the instructions may be executed simultaneously, serially, or otherwise executed by one or multiple processors.

While several embodiments have been provided in the present disclosure, it should be understood that the disclosed systems and methods may be embodied in many other specific forms without departing from the spirit or scope of the present disclosure. The present examples are to be considered as illustrative and not restrictive, and the intention is not to be limited to the details given herein. For example, the various elements or components may be combined or integrated in another system or certain features may be omitted or not implemented.

Also, techniques, systems, subsystems, and methods described and illustrated in the various embodiments as discrete or separate may be combined or integrated with other systems, modules, techniques, or methods without departing from the scope of the present disclosure. Other items shown or discussed as directly coupled or communicating with each other may be indirectly coupled or communicating through some interface, device, or intermediate component, whether electrically, mechanically, or otherwise. Other examples of changes, substitutions, and alterations are ascertainable by one skilled in the art and could be made without departing from the spirit and scope disclosed herein.

What is claimed is:

1. An automated method of setting of appointments for health care services, comprising:
   receiving, by a computer, a health care service request from a first health care service requester, the health care service request including a description of symptom;
   determining, by the computer, an urgency of the health care service request based on the description of symptoms;
   performing by the computer a pre-diagnosis interaction with the first health care service requester, wherein the pre-diagnosis interaction comprises:
      querying a second set of information from the first health care service requester,
      receiving at least one response comprising the second set of information from the first health care service requester, wherein the second set of information includes at least one of a duration of the symptom, a trend in the symptom, and an acuity of the symptom,
      analyzing by the computer the at least one response provided by the first health care service requester,
      applying weights to the at least one response, and
      consulting at least one diagnostic database;
   identifying, by the computer, candidate health care service appointments based on searching a database of health care service offerings using a location filter, the preferences received, the urgency of the health care service request, and the at least one response;
   communicating, by the computer, to the health service requester appointment choices for health care service offerings;
   receiving, by the computer, a choice of appointment;
   confirming, by the computer, the chosen appointment;
   monitoring, by the computer, a plurality of health care resources across time slots and facilities;
   identifying, by the computer, an opportunity to change one or more appointments to more efficiently use the health care resources;
   determining by the computer a second health care service requester to offer an incentive to based on historical information about the willingness, inclination, or propensity of the second health care service requester to change a previously booked appointment and the types of incentives used to induce the second health care service requester to accept an appointment change;
   determining, by the computer, a financial incentive to tender to the second health care requester as an inducement to change an appointment of the second health care requester based on the historical information, the value of the financial incentive related to the benefit presented by the opportunity to change the appointment, wherein the financial incentive comprises at least one of a waiver of a co-payment and a reduction of a co-payment; and
   communicating, by the computer, to the second health care requester, the financial incentive to change the appointment based on load balancing across time slots and facilities and further based on adjusting an overbooked condition of a health care service provider.

2. The method of claim 1, wherein the health care service request is received electronically via an internet using one of a simple mail transport protocol and a hypertext transfer protocol.

3. The method of claim 1, wherein identifying the candidate health care service appointments based on searching the database of health care service offerings is further based on comparing the preferred appointment time with an availability schedule of the health care service offerings and comparing a location of an office associated with the health care service offerings with a location preference.

4. The method of claim 3, wherein the comparing the location of the office associated with the health care service offerings with a location preference is based on a maximum radius preference.

5. The method of claim 3, wherein the identifying the candidate health care service appointments is based on identifying candidates that match a maximum number of preferences and the location filter.

6. The method of claim 1 wherein confirming the choice of appointment comprises sending notification to a health care provider and a patient associated with the health care request.

7. The method of claim 1, wherein the financial incentive to change the appointment is associated with changing at least one of a provider facility location, a time, and a date of the health care service appointment.

8. The method of claim 1, wherein identifying the opportunity to change the appointment is based on analyzing a patient profile to estimate willingness to accept the financial incentive to change the schedule of the health care service appointment and wherein communicating the financial incentive to change the appointment comprises sending a message containing information about the financial incentive to a patient associated with the appointment.

9. The method of claim 1, wherein the financial incentive further comprises at least one of a coupon and a discount.

* * * * *